United States Patent [19]

Lerman et al.

[11] Patent Number: 5,874,620
[45] Date of Patent: Feb. 23, 1999

[54] PROCESS FOR THE PURIFICATION OF (RR-SS)-2-DIMETHYLAMINOMETHYL-1-(3-METHOXYPHENYL)CYCLOHEXANOL HYDROCHLORIDE

[75] Inventors: Ori Lerman, Ramat Gan; Joseph Kaspi, Givatayim; Dov Brenner, Lod, all of Israel

[73] Assignee: Chemagis, Ltd., Bnei Brak, Israel

[21] Appl. No.: 911,518

[22] Filed: Aug. 14, 1997

[30] Foreign Application Priority Data

Aug. 22, 1996 [IL] Israel ........................................ 119121

[51] Int. Cl.⁶ .................................................. C07C 209/88
[52] U.S. Cl. .......................... 564/443; 564/304; 564/424; 564/437
[58] Field of Search ...................... 564/304, 424, 564/437, 443

[56] References Cited

U.S. PATENT DOCUMENTS 3,652,589  3/1972  Flick ........................................ 548/578

*Primary Examiner*—Richard L. Raymond
*Attorney, Agent, or Firm*—Darby & Darby

[57] ABSTRACT

The invention provides a process for the separation of (RR,SS) 2-dimethylaminomethyl-1-(3-methoxyphenyl) cyclohexanol hydrochloride [(RR,SS)-Tramadol], from a mixture consisting of (RR,SS) Tramadol and (RS,SR)-2-dimethylaminomethyl-1-(3-methoxyphenyl) cyclohexanol [(RS,SR)-Tramadol], which process includes combining the mixture with an electrophilic reagent, the reagent selectively reacting with the hydroxyl group of (RS,SR)-Tramadol, leaving most of the (RR,SS) Tramadol intact, and precipitating the remaining, practically pure (RR,SS) Tramadol from the mixture.

9 Claims, No Drawings

PROCESS FOR THE PURIFICATION OF (RR-SS)-2-DIMETHYLAMINOMETHYL-1-(3-METHOXYPHENYL)CYCLOHEXANOL HYDROCHLORIDE

FIELD OF THE INVENTION

The present invention relates to a process for the purification of (RR,SS)-2-dimethylaminomethyl-1-(3-methoxyphenyl)cyclohexanol hydrochloride, also known as trans Tramadol, from its (RS,SR) isomer and from other undesirable products.

More particularly, the present invention relates to a process for the purification of the (RR,SS) isomer, based on the discovery that the hydroxyl group of the (RS,SR) isomer undergoes various chemical reactions faster than the same group of the (RR,SS) isomer. Thus, the invention is based on reacting a mixture of isomers with various chemical substances reacting predominantly with the (RS,SR) isomer, while the (RR,SS) isomer remains practically intact. The desired (RR,SS) isomer is then easily purified by recrystallization from an appropriate solvent.

BACKGROUND OF THE INVENTION

Tramadol is a well established pain killer, invented by Gruenenthal GmbH, Germany, used as a non-addictive analgesic and sold under different trade names such as Tramal, Ultram, Crispin and Tramundin.

The synthesis of Tramadol is described in U.S. Pat. No. 3,652,589 and in British Patent No. 992,399. The synthesis of Tramadol consists of a Grignard reaction between 2-dimethylaminomethylcyclohexanone and 3-methoxyphenyl magnesium bromide (Equation 1). From the reaction scheme, it is clear that both isomers (RR,SS) (Structure 1) and (RS,SR) (Structure 2) are obtained in variable ratios, depending on the reaction conditions.

EQUATION 1

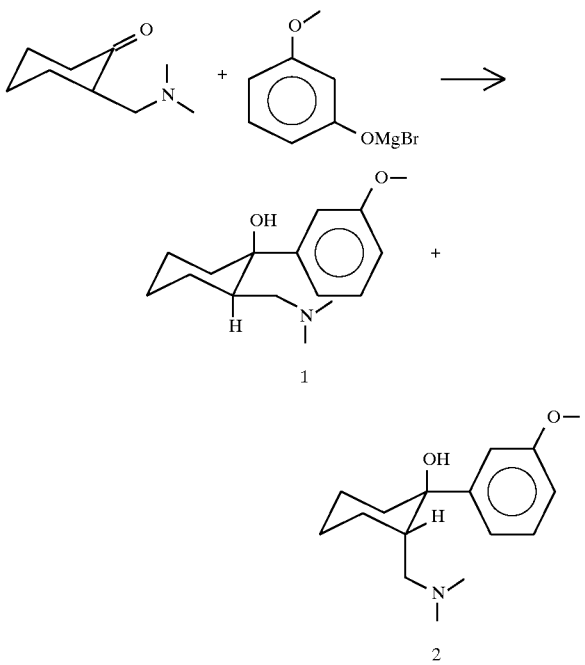

The original patents assigned to Gruenenthal GmbH describe the isolation of the (RR,SS) isomer, as follows:

The complex mixture of products containing both isomers of Tramadol obtained from the Grignard reaction is distilled under reduced pressure. The isomers are distilled together at 138°–140° C. (0.6 mm Hg). The distillate is dissolved in ether and is reacted with gaseous HCl. The resulting mixture of both isomers of Tramadol is precipitated as hydrochlorides and filtered. The resulting mixture contains about 20% of the (RS,SR) isomer. The isomer mixture is then refluxed twice with five volumes of moist dioxane, and filtered. The cake obtained consists of pure (RR,SS) isomer. The residual solution consists of "a mixture of about 20–30% of the cis (i.e. RS,SR), which cannot be further separated by boiling dioxane" [U.S. Pat. No. 3,652,589, Example 2].

Dioxane, used in large quantities in this process, possesses many undesirable properties. It has recently been listed as a Category I carcinogen by OSHA [Kirk & Othmer, 3rd Ed., Vol. 9, p. 386], and it is known to cause CNS depression and liver necrosis [ibid., Vol. 13, p. 267]; in addition, it tends to form hazardous peroxides [ibid., Vol 17, p. 48]. As a result, the concentration of dioxane in the final product has been strictly limited to several ppb's, and the DAC (1991) restricted the level of dioxane in Tramadol to 0.5 ppm.

A different separation method, described in Israeli Specification No. 103096, takes advantage of the fact that the precipitation of the (RR,SS) isomer of Tramadol from its solution in medium chained alcohols ($C_4$–$C_8$) occurs faster than the precipitation of the (RS,SR) isomer, which tends to separate later. The main disadvantage of this method is, that the time interval between the end of separation of the (RR,SS) isomer and the beginning of the (RS,SR) isomer separation is variable, and seems to depend sharply on the composition of the crude mixture. Therefore, variations in the yield and the quality of the product often occur. Furthermore, about 40% of the (RR,SS) isomer does not separate and remains in solution, along with the (RS,SR) isomer. This remaining mixture cannot be further purified by this method.

Another method, described in Israeli Specification No. 116281, relies on the fact that the (RS,SR) isomer of Tramadol undergoes dehydration much faster then the (RR,SS) isomer, when treated with 4-toluenesulfonic acid, or sulfuric acid; furthermore, when the reaction is carried out in an aqueous medium, a certain amount (up to 50%) of the (RS,SR) isomer is converted to the (RR,SS) isomer. This may, of course increase the efficiency of the process.

The unreacted (RR,SS) isomer is then separated from the dehydrated products and from other impurities by simple crystallization.

While further examining the results of the latter process, it was surprisingly found that the hydroxyl group of the (RS,SR) isomer of Tramadol reacts faster than the same group of the (RR,SS) with various reagents. A plausible explanation for this observation can be supplied by comparing the structures of both isomers, and their ability to form hydrogen bonds.

Looking closely at FIG. 1 [(RR,SS) Tramadol hydrochloride] and at FIG. 2 [(RS,SR) Tramadol hydrochloride], one can provide a plausible explanation for the difference in the OH group's activity, as follows: The proton attached to the nitrogen atom of the protonated (RR,SS) isomer of Tramadol is capable of forming a stable hydrogen bonding with the oxygen atom of the hydroxyl group (see FIG. 1). Thus, any reaction involving protonation of the hydroxyl group (such as dehydration), or any reaction in which the hydroxyl group reacts as a nucleophile (such as a nucleophilic substitution or esterification process) is less favored to occur.

In the (RS,SR) isomer, on the other hand, there is no possible way of forming a stable intramolecular hydrogen bond, and therefore, any of the above-mentioned types of reactions can easily occur, considering the fact that this particular hydroxyl group is tertiary and benzyllic.

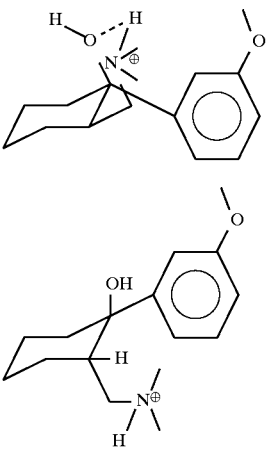

figure 1

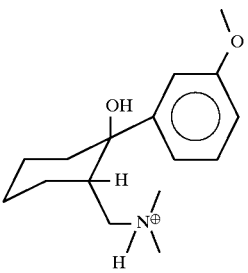

figure 2

The general purification procedure of the present invention consists of reacting a mixture of both geometrical isomers of Tramadol hydrochloride with a potential electrophile under such conditions that the (RS,SR) isomer reacts almost exclusively, while the (RR,SS) isomer remains practically intact. The resulting mixture is evaporated and the resulting solid substance is then recrystallized from isopropanol or any other suitable solvent.

SUMMARY OF THE INVENTION

Thus, according to the present invention, there is now provided a process for the separation of (RR,SS)-2-dimethylaminomethyl-1-(3-methoxyphenyl) cyclohexanol hydrochloride [(RR,SS)-Tramadol], from a mixture consisting of (RR,SS)-Tramadol and (RS,SR)-2-dimethylaminomethyl-1-(3-methoxyphenyl) cylcohexanol [(RS,SR)-Tramadol], comprising combining said mixture with an electrophilic reagent, said reagent selectively reacting with the hydroxyl group of (RS,SR)-Tramadol, leaving most of the (RR,SS)-Tramadol intact, and precipitating the remaining, practically pure (RR,SS)-Tramadol from said mixture.

In a first preferred embodiment of the present invention, said electrophilic reagent is an acetylating agent, preferably acetic anhydride.

In a second preferred embodiment of the present invention, said electrophilic reagent is a halogen-providing substitution agent, preferably chlorine. An especially preferred agent is thionyl chloride.

In another preferred embodiment of the present invention, there is provided a process for the separation of a mixture consisting of (RR,SS)-2-dimethylaminomethyl-1-(3-methoxyphenyl)cyclohexanol hydrochloride and (RS,SR)-2-dimethylaminomethyl-1-(3-methoxyphenyl)cyclohexanol hydrochloride, comprising selectively reacting said (RS,SR) isomer with a salt of hydrazoic acid in acidic medium; neutralizing the resulting solution; precipitating the remaining practically pure (RR,SS) Tramadol with hydrogen chloride from an alcoholic solution; and purifying the precipitated (RR,SS) isomer by recrystallization.

In another preferred embodiment of the invention, said reaction is carried out with sodium azide in the presence of trifluoroacetic acid.

More particularly, the above-mentioned isomer mixture is reacted with acetic anhydride, thionyl chloride or hydrazoic acid; 1-acetoxy-1-(3-methoxyphenyl)-2-dimethylaminomethyl cyclohexane, 1-chloro-1-(3-methoxyphenyl)-2-dimethylaminomethyl cyclohexane, and 1-azido-1-(3-methoxyphenyl)-2-dimethylaminomethyl cyclohexane (as the hydrochloride salts) are respectively formed, mainly originating from the more reactive (RS,SR) isomer, as shown in Equation 2:

EQUATION 2

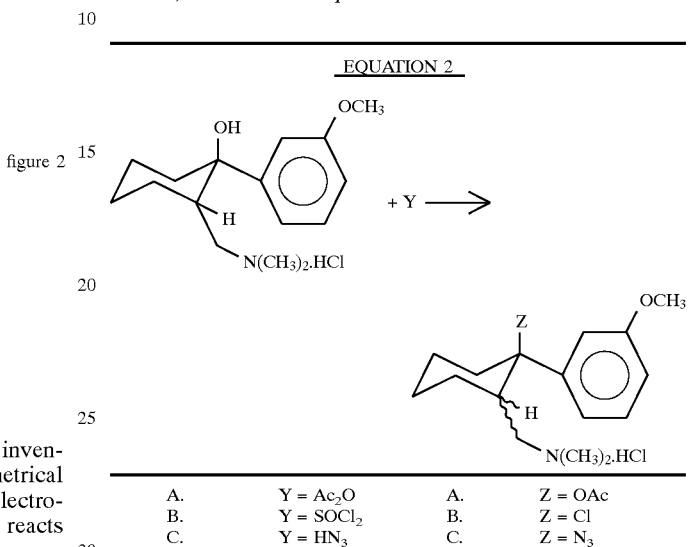

| A. | Y = Ac$_2$O | A. | Z = OAc |
| B. | Y = SOCl$_2$ | B. | Z = Cl |
| C. | Y = HN$_3$ | C. | Z = N$_3$ |

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

11.1 g of a mixture consisting of 77% (RR,SS) Tramadol hydrochloride and 23% of the corresponding (RS,SR) isomer were dissolved in 30 ml DMF. 1.3 g acetic anhydride were added and the reaction mixture was stirred at room temperature for 12 hours. The solvent was partly evaporated under reduced pressure and 15 ml toluene were added. The suspension obtained was filtered and washed with 5 ml toluene. 5.8 g of crystals were obtained, in which the (RR,SS):(RS,SR) isomer ratio was 70:1. The product obtained was crystallized from 12 ml isopropanol and 4 g of pure (RR,SS) Tramadol hydrochloride were obtained.

EXAMPLE 2

19.5 g of a mixture consisting of 60.5% (RR,SS) Tramadol hydrochloride and 40.5% of the corresponding (RS,SR) isomer were suspended in 55 ml chlorobenzene. A solution of 4 ml thionyl chloride in 15 ml chlorobenzene was added dropwise for two hours. The suspension was partly evaporated, the residue was filtered and rinsed with toluene, and 8.1 g of crystals were obtained, in which the (RR,SS):(RS,SR) isomer ratio was 14:1. The product obtained was recrystallized from isopropanol, and 6.7 g of pure (RR,SS) Tramadol hydrochloride were obtained.

EXAMPLE 3

33.4 g of a mixture consisting of 45% (RR,SS) Tramadol hydrochloride and 55% of the corresponding (RS,SR) isomer was immersed in 50 ml trifluoroacetic acid, 5.2 g of sodium azide was added, and the reaction mixture was stirred for 24 hours. The reaction mixture was then evaporated under reduced pressure, 50 ml water was added, and the solution was brought to pH 12 with solid potassium carbonate. The suspension was extracted with 50 ml toluene, the solvent was evaporated and 25 ml hydrogen chloride solution in isopropanol were added. The solution was cooled and filtered. 9.5 g of crude (RR,SS) Tramadol were obtained, and the crude product was purified by recrystallization from isopropanol. The hitherto unknown (RS,SR)-2-(dimethylaminomethyl)-1-azido-1-(3-methoxyphenyl)-cyclohexane hydrochloride was isolated from the reaction mixture, recrystallized from isopropanol and characterized as follows:

ms: 288 m+

IR: 2050 cm$^{-1}$ ($N_3$)

$^1$H-NMR (DMSO): 10.42 ppm: (acidic proton); 1H; 7.40–6.90 ppm: (aromatic protons) 4H; 3.79 ppm; (OC$\underline{H}_3$), 3H; 2.78, 2.42 ppm: NC$\underline{H}_2$; 2H; 2.58, 2.37 ppm: [N(C$\underline{H}_3$)$_2$], 6$\underline{H}$; 2.30–1.40 ppm: cyclohexane ring protons, 9H.

$^{13}$CNMR (DMSO): 159.74 ppm: $C_1$; 144.12 ppm: $C_5$; 130.08 ppm: $C_3$; 117.36 ppm: $C_4$; 112.97, 111.35 ppm: $C_2$, $C_6$; 69.61 ppm: $C_8$; 59.29 ppm: $C_{14}$; 55.21 ppm: $C_7$; 44.6 ppm: $C_{15}$; 40.12 ppm: $C_{13}$; 35.94, 27.02, 23.56, 21.63 ppm: cyclohexane ring carbon nuclei.

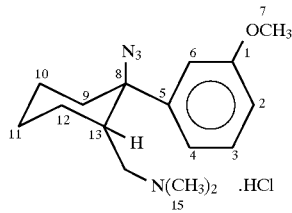

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the separation of (RR,SS) 2-dimethylaminomethyl-1-(3-methoxyphenyl) cyclohexanol hydrochloride [(RR,SS)-Tramadol], from a mixture consisting of (RR,SS) Tramadol and (RS,SR)-2-dimethylaminomethyl-1-(3-methoxyphenyl) cyclohexanol [(RS,SR)-Tramadol], comprising:

combining said mixture with an electrophilic reagent, said reagent selectively reacting with the hydroxyl group of (RS,SR)-Tramadol, leaving most of the (RR,SS) Tramadol intact, and precipitating the remaining, practically pure (RR,SS) Tramadol from said mixture.

2. A process according to claim 1, wherein said precipitated (RS,SR) isomer is further purified by recrystallization.

3. A process according to claim 1, wherein said electrophilic reagent is an acylating agent.

4. A process according to claim 3, wherein the acylating agent is acetic anhydride.

5. A process according to claim 1, wherein said electrophilic reagent is a halogen-providing substitution agent.

6. A process according to claim 5, wherein said halogen atom is chlorine.

7. A process according to claim 5, wherein said substitution agent is thionyl chloride.

8. A process according to claim 1 for the separation of a mixture consisting of (RR,SS)-2-dimethylaminomethyl-1-(3-methoxyphenyl) cyclohexanol hydrochloride and (RS,SR)-2-dimethylaminomethyl-1-(3-methoxyphenyl) cyclohexanol hydrochloride, comprising:

selectively reacting said (RS,SR) isomer with a salt of hydrazoic acid in acidic medium;

neutralizing the resulting solution;

precipitating the remaining practically pure (RR,SS) Tramadol with hydrogen chloride from an alcoholic solution; and purifying the precipitated (RR,SS) isomer by recrystallization.

9. A process according to claim 8, wherein said reaction is carried out with sodium azide in the presence of trifluoroacetic acid.

* * * * *